United States Patent [19]

Novotny

[11] 4,283,582

[45] Aug. 11, 1981

[54] PRE-PRESSURING METHANOL-COBALT WITH CARBON MONOXIDE IN HOMOLOGATION OF METHANOL

[75] Inventor: Miroslav Novotny, Denville, N.J.

[73] Assignee: Allied Chemical Corporation, Morris Township, Morris County, N.J.

[21] Appl. No.: 884,064

[22] Filed: Mar. 6, 1978

[51] Int. Cl.$^3$ .................. C07C 27/00; C07C 29/36
[52] U.S. Cl. ........................................... 568/902
[58] Field of Search ..................................... 568/902

[56] References Cited

U.S. PATENT DOCUMENTS 3,285,948  11/1966  Butter .................................. 568/902

Primary Examiner—Joseph E. Evans
Attorney, Agent, or Firm—Alan M. Doernberg; Gerhard H. Fuchs

[57] ABSTRACT

An improved process is described for synthetically converting methanol to ethanol in which a mixture of methanol and cobalt catalyst is pre-pressurized with an atmosphere of carbon monoxide at room temperature and at a pressure of about 10 to 1000 psi gauge, in a suitable pressure vessel. A gaseous mixture of carbon monoxide/hydrogen, in the stoichiometric 1:2 molar ratio, is then introduced to react with the methanol/cobalt catalyst mixture and the temperature is raised to about 175° to 240° C. at a pressure of about 3000–6000 psig. The improved process leads to higher selectivities of ethanol formation with lowered amounts of by-products.

4 Claims, 2 Drawing Figures

DEPENDENCE OF SELECTIVITY AND CONVERSION ON THE INITIAL CO PRESSURE.

SELECTIVITY TO ETHANOL (———); CONVERSION OF METHANOL (—·—·—·—).

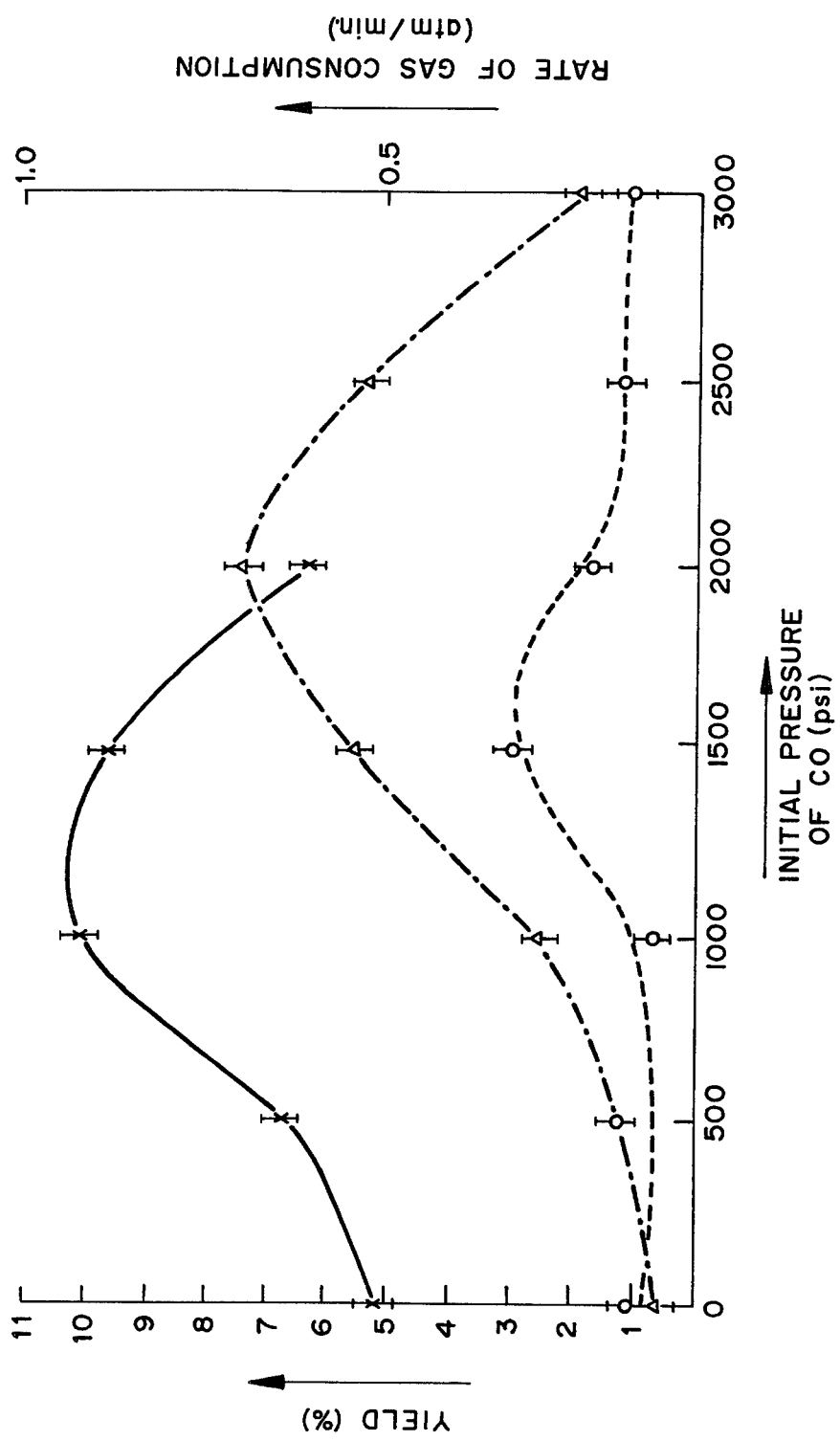
FIG. 2 DEPENDENCE OF THE RATE OF GAS CONSUMPTION (CO/2H$_2$) AND THE YIELD OF METHYL ACETATE AND ETHYL ACETATE ON THE INITIAL CO PRESSURE.
RATE OF GAS CONSUMPTION (———); METHYL ACETATE (—··—); ETHYL ACETATE (-----).

PRE-PRESSURING METHANOL-COBALT WITH CARBON MONOXIDE IN HOMOLOGATION OF METHANOL

BACKGROUND OF THE INVENTION

1. Field of the Invention

This invention relates to an improved process for producing ethanol from methanol by reacting a mixture of methanol and cobalt catalyst, under a carbon monoxide atmosphere, with a gaseous mixture of carbon monoxide/hydrogen.

2. Brief Description of the Prior Art

Ethanol is a well-known organic chemical and has a wide variety of industrial applications including use as a solvent for resins, fats and fatty acids and serves as a "building block" for the synthesis of a variety of larger molecular weight organic compounds.

The overall process of converting an organic compound to a higher homologue, by increasing the number of $CH_2$ units by one, is termed in the art, "homologation".

Processes for homologating methanol to ethanol are known in the art and provide a potential basis for the synthetic production of ethanol to supplement ethanol obtained by fermentation.

The reference Science, Vol. 113, pp. 206-207 (1951), describes the reaction of methanol and dicobalt octacarbonyl with a 1:1 molar mixture of carbon monoxide/hydrogen at a pressure in the range from 2410 to 5100 psi gauge and a temperature of about 183° to 185° C. A 77% methanol conversion was achieved with only a 38% selectivity towards ethanol. However, higher selectivities are required, for example of above about 45%, before such a process is seriously considered to be commercially attractive.

Other prior art processes, as exemplified in British Pat. No. 951,506 (1964), U.S. Pat. No. 3,248,432 (1966), U.S. Pat. No. 3,285,948 (1966) and Belgian Pat. No. 842,430 (1966), utilize secondary promoter reagents such as iodine, phosphorus compounds, ruthenium and osmium halides and tertiary phosphine for increasing the selectivity of ethanol production during the homologation of methanol. However, these secondary promoter reagents usually increase the cost of such a process and may introduce complicating factors into the ethanol isolation and purification steps.

SUMMARY OF THE INVENTION

We have found that ethanol can be produced in good yield and selectivity from the homologation of methanol in the absence of secondary promoters such as iodine and phosphorus compounds by the novel step of pre-pressurizing a methanol-cobalt catalyst mixture with a carbon monoxide atmosphere, in an amount corresponding to a pressure of about 10 to 1000 psi gauge at room temperature, and maintaining said atmosphere of carbon monoxide while introducing a 1:2 molar mixture of carbon monoxide/hydrogen gas, $CO/2H_2$, and then raising the temperature to about 175° C. to 240° C. at a pressure of about 3000-6000 psig.

In accordance with this invention there is provided an improved process for converting methanol to ethanol including contacting a mixture of methanol and cobalt catalyst with a gaseous mixture of carbon monoxide and hydrogen gas, in about a 1:2 molar ratio, respectively, and allowing the combined mixtures to react at a temperature of about 175° to 240° C. and a pressure of about 3000-6000 psig, wherein the improvement comprises pre-pressurizing the methanol/cobalt catalyst mixture with an atmosphere consisting essentially of carbon monoxide in an amount corresponding to a pressure of about 10 to 1000 psi gauge, at room temperature, or its equivalent at other temperatures, and maintaining said atmosphere of carbon monoxide while introducing with said carbon monoxide/hydrogen gaseous mixture.

BRIEF DESCRIPTION OF THE DRAWINGS

FIG. 2 is a plot of percent yield of methyl and ethyl acetates and rate of gas consumption versus initial pressure of carbon monoxide in psi gauge, at room temperature, obtained as data from the same above-mentioned runs described in the Example. The curves illustrate the dependence of the rate of gas consumption and the yields of methyl acetate and ethyl acetate upon the initial carbon monoxide pressure.

DETAILED DESCRIPTION OF THE INVENTION AND THE PREFERRED EMBODIMENTS

Figure 1:
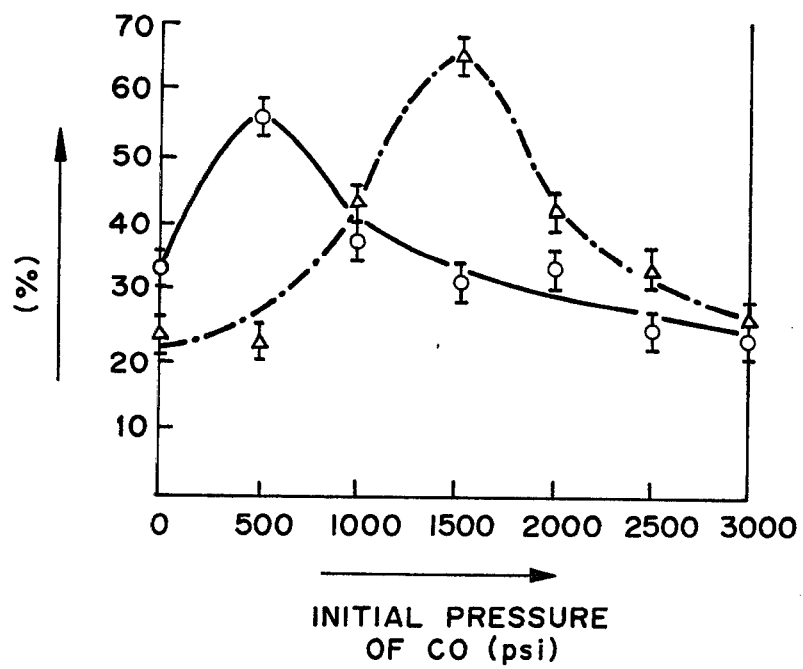
FIG. 1 is a plot of percent selectivity of ethanol production and percent conversion of methanol versus initial pressure of carbon monoxide in psi gauge, at room temperature, obtained as data from the runs described in the following Example. The curves illustrate the dependence of the selectivity of ethanol production and methanol conversion upon the initial carbon monoxide pressure.

The overall process of this invention can be represented by the following equation:

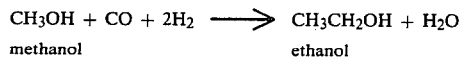

$$CH_3OH + CO + 2H_2 \longrightarrow CH_3CH_2OH + H_2O$$
$$\text{methanol} \qquad\qquad\qquad\quad \text{ethanol}$$

The novel aspect of this invention is the discovery that pre-pressurizing the methanol-cobalt catalyst mixture with a carbon monoxide atmosphere, prior to reaction with the indicated stoichiometric gaseous carbon monoxide-hydrogen mixture, significantly increases the selectivity of the process toward production of ethanol. Thus, the necessity of using promoters such as iodine or phosphorous type compounds is eliminated. By the term "prepressurization" as used herein, is meant the step of initially contacting the liquid mixture with a pressurized atmosphere, greater than one atmosphere, consisting essentially of carbon monoxide. This step is a novel departure form processes in the prior art where different gaseous ratios of $CO/H_2$ are initially charged into the reactor. In such processes, carbon monoxide and hydrogen are absorbed and consumed in the stoichiometric 1:2 molar ratio in accordance with the above equation. Where non-stoichiometric ratios of carbon monoxide and hydrogen are used, the resulting gaseous mixture inside the reactor is slowly enriched with respect to one of the components undesirably leading either to the precipitation of cobalt metal (in the case where the mixture is richer in hydrogen than the stoichiometric mixture) or oversaturation of the catalyst with carbon monoxide (where the mixture is richer in carbon monoxide than the stoichiometric mixture). In the above situations the reaction is either prematurely terminated or large amounts of undesirable by-products are formed. Where the stoichiometric mixture is used, in the absence of a prepressurization step, the selectivity for ethanol production is low.

As seen in FIG. 1, high selectivities are obtained, with respect to percent conversion of methanol, when initial atmospheres of carbon monoxide of up to 1000 psi gauge are used. Higher initial pressures than 1000 psi lead to lower selectivities for ethanol production and greater amounts of by-products, while lower initial pressures than 10 psi gauge, at room temperature, lead to lower selectivities of ethanol production. The mechanism whereby pre-pressurizing the methanol-cobalt catalyst mixture increases the selectivity of the process toward ethanol production is not clearly understood but is thought to relate to the formation of a complex carbon monoxide-catalyst species which specifically directs the process toward the production of ethanol.

In general, an amount of carbon monoxide corresponding to a pressure of about 10 to 1000 psi gauge at room temperature, or its equivalent at other temperatures, is necessary in the pre-pressurization step to effect good yields and high selectivities of ethanol production in the reaction. A preferred range of carbon monoxide is an amount corresponding to a pressure of about 250 to 1000 psi gauge at room temperature, or its equivalent at other temperatures, and a particularly preferred range is an amount corresponding to a pressure of about 400 to 750 psi gauge at room temperature, or its equivalent at other temperatures. After pre-pressurizing the methanol-cobalt catalyst mixture, the amount of carbon monoxide introduced during pre-pressurization is maintained while the stoichiometric carbon monoxide/hydrogen gaseous mixture is introduced in portions throughout the reaction process. The reason the initial amount of carbon monoxide is maintained, is because only the stoichiometric gaseous mixture of $CO/2H_2$ is consumed during the reaction, while the excess carbon monoxide remains to maintain the catalyst activity. It is preferred to effect the pre-pressurization of carbon monoxide at room temperature. However, lower or higher temperatures can be used for the pre-pressurization step with the limitation that an amount of carbon monoxide equivalent to 10 to 1000 psi gauge at room temperature is employed.

The pre-pressurizing step is conducted with an atmosphere consisting essentially of carbon monoxide, but small percentages of other gases such as hydrogen, nitrogen or carbon dioxide present in amounts of up to about 10 volume percent can be tolerated. It is preferred to use a carbon monoxide atmosphere comprised of about 99% carbon monoxide.

Cobalt catalysts employed in the reaction can be any conventional type employed in the prior art including soluble and partially insoluble catalysts. Representative catalysts include dicobalt octacarbonyl, cobalt acetate, cobalt oxide, cobalt chloride, cobalt iodide and the like. A preferred catalyst is cobalt octacarbonyl, $[Co(CO)_4]_2$. In addition, metal co-catalysts may be used with the cobalt catalyst and are meant to be included in the term "mixture of methanol and cobalt catalyst." Representative examples include ruthenium, rhodium, osmium, iridium, iron and the like. Usually an amount of metal co-catalyst of about 0.01 to 1 part co-catalyst per part of cobalt catalyst is employed. If employed, preferred metal catalyst is ruthenium.

Although not required as in the prior art, promoter agents such as iodine, iodide salts and phosphorus-type compounds may also be used if desired.

The concentration of catalyst used in the methanol is in the range used in the prior art and is usually an amount of about 0.01 to 0.02 parts of cobalt catalyst per part of methanol.

The temperature of the process is usually conducted in a range used in the prior art and is usually about 175° C. to 240° C.

The reaction pressure, i.e., the pressure at which the carbon monoxide/hydrogen mixture is reacted with the methanol-cobalt catalyst mixture under carbon monoxide atmosphere, is usually in the range of about 3000 to 6000 psi gauge (psig) at reaction temperature.

The selectivity of ethanol production, $100 \times$ (moles ethanol produced $\div$ moles methanol converted) is generally in the range of about 35 to 65% and the percent conversion of methanol in the process is usually about 25 to 70%.

In general, by-products in the reaction include methyl acetate, ethyl acetate, small amounts of acetaldehyde, ethers, methane and carbon dioxide.

In the reaction, methanol is much more readily homologated than is ethanol, and thus, formed ethanol can be obtained in good yield and selectivity from the process. Pure ethanol can be obtained from the reaction mixture by subjecting it to conventional purification techniques such as fractional distillation.

Apparatus which is useful in the process can be any conventional type of pressure reactor apparatus, equipped with means for introducing a gaseous mixture, a heating element and a mixing or rocking element. Such apparatus is well known in the art.

The following examples are illustrative of the best mode of carrying out the invention as contemplated by us but should not be construed as being limitations on the scope or spirit of the instant invention.

EXAMPLE I

Seven runs were conducted using the following general procedure: Into a 183 ml. volume reactor (316 SS) rocker pressure apparatus, 1.54 grams of dicobalt octacarbonyl was charged, under a nitrogen atmosphere, with 20 grams of commercial grade methanol which was previously degassed. The reactor in each run, having about 160 ml. free volume, was pre-pressurized with carbon monoxide atmospheres at pressures of 500, 1000, 1500, 2000, 2500 and 3000 psi gauge at room temperature, respectively, and the internal pressure in each run was then adjusted with a 1:2 mixture of carbon monoxide/hydrogen to an initial room temperature reaction pressure of 3000 psi gauge (1 psi = 6.89 kPa). A comparative run, Run 1, was not pre-pressurized with carbon monoxide, but was charged with the stoichiometric 1:2 carbon monoxide/hydrogen gaseous mixture at room temperature to the same initial reaction pressure of 3000 psi gauge. After the initial reaction pressure at room temperature was adjusted to 3000 psi gauge, heat was applied to each run and when an internal temperature of about 170° C. was reached, more $CO/2H_2$ mixture was added to increase the internal pressure to 5000 psi. When the internal temperature of the reactor reached 185° C., rocking of the reactor was started. This was also considered as the beginning of the homologation reaction, which was carried out for a total of 4 hours for each run. The internal pressure of the vessel, during this period, was maintained at 4700 psi to 5400 psi by additions of the stoichiometric amount of $CO/2H_2$ mixture. After the 4 hour reaction period, the reactor was cooled and vented, and the reaction mixture from each run was analyzed by a Hewlett-Packard, 5710A gas chromatograph equipped with a Porapack P column. The results of the seven runs are tabulated below in TABLE I.

The results of the two runs are tabulated below in TABLE II. The headings used are the same as in TABLE I.

| Run | Pre-Pressurization pressure (psig) | $Y_{EtOH}$ | $S_{EtOH}$ | $Y_{MeOAc}$ | $Y_{EtOAc}$ | $R_1\left(\dfrac{atm.}{min.}\right)$ | $C_{MeOH}$ |
|---|---|---|---|---|---|---|---|
| 1 | CO/2H$_2$ mixture | 8 | 33 | 0.61 | 1.05 | 0.52 | 24 |
| 2 | 500 CO | 13 | 56 | 1.26 | 1.28 | 0.67 | 23 |
| 3 | 1000 CO | 16 | 37 | 2.49 | 0.62 | 1.07 | 43 |
| 4 | 1500 CO | 20 | 31 | 5.51 | 2.95 | 0.96 | 64 |
| 5 | 2000 CO | 14 | 33 | 7.36 | 1.65 | 0.63 | 42 |
| 6 | 2500 CO | 9 | 26 | 5.21 | 0.91 | —(a) | 31 |
| 7 | 3000 CO | 6 | 23 | 1.84 | 0.87 | —(a) | 26 |

(a) measurements of the rate were not conducted due to the comparatively slow rate of observed gas consumption.

The headings in the Table are described as follows:
1. (psig) is pounds per square inch gauge at room temperature.
2. $Y_{ETOH}$ (percent yield of ethanol), is (moles ethanol produced ÷ moles methanol introduced) × 100.
3. $S_{ETOH}$ (selectivity of ethanol production), is (moles ethanol produced ÷ moles methanol converted) × 100.
4. $Y_{MeOAc}$ (percent yield of methyl acetate), is (moles of methyl acetate produced ÷ moles of methanol introduced) × 100.
5. $Y_{EtOAc}$ (percent yield of ethyl acetate), is (moles of ethyl acetate produced ÷ moles of methanol introduced) × 100.
6. $R_1\left(\dfrac{atm.}{min.}\right)$ is the rate of CO/2H$_2$ gas consumption, in atmospheres/minute, during the first hour of each run.
7. $C_{MeOH}$ (percent conversion of methanol), is (moles methanol reacted ÷ moles methanol introduced × 100).

The results of the seven runs in terms of percent conversion of methanol and percent yield of ethanol, based on the amount of methanol converted are also illustrated as triangular points and circular points, respectively, in FIG. 1. The yield and conversion values can be read directly for each run above the initial pressure of CO used in the run as the abscissa.

The data indicate that a partial pressure of carbon monoxide, higher than that required by the stoichiometry of the above equation of the overall process, is beneficial for the selectivity towards ethanol production in the homologation reaction. An initial carbon monoxide pressure of about 500 psi at room temperature probably generates the most favorable conditions for the selective formation of ethanol.

The percent yields of methyl acetate and ethyl acetate based on amount of methanol converted and rates of gas (CO/2H$_2$) consumption as a function of initial pressure of CO at room temperature, measured during the first hour, are illustrated as triangular points, circular points, and "X" points, respectively, in FIG. 2. The yields of methyl acetate, ethyl acetate and rate of gas consumption in atmospheres/minute, can be read directly for each run above the initial pressure of CO used in the run as the abscissa.

EXAMPLE II

Two runs were made, following the general procedure described in Example I, except that the initial room temperature reaction pressure in the reactor was adjusted to 4000 psi gauge before heating. A pressure of about 5100–5700 psi gauge was maintained during the 4 hour reaction period at 185° C., by the addition of 1:1 CO/H$_2$ in Run 1 and the addition of 1:2 CO/H$_2$ in Run 2.

TABLE II

| Run | Pre-Pressurization Pressure (psig) | $Y_{ETOH}$ | $C_{MeOH}$ | $S_{ETOH}$ |
|---|---|---|---|---|
| 1 | CO/H$_2$ | 29.3 | 62.3 | 46.8 |
| 2 | 500 CO | 17.6 | 49.5 | 58.6 |

The data indicates that higher selectivity for ethanol formation is achieved by pre-pressurizing the reaction mixture with 500 psi gauge of CO, followed by addition of the stoichiometric mixture of CO/2H$_2$ to an initial pressure of 4000 psi gauge, before reaction, as opposed to subjecting the reaction mixture to an amount of 1:1 CO/H$_2$ mixture equivalent to 4000 psi gauge before reaction. Thus, with a given initial room temperature reaction pressure in the reactor prior to reaction, e.g., 3000 or 4000 psi gauge, pre-pressurizing with an amount of carbon monoxide equivalent to a pressure of about 10–1000 psi gauge, and preferably about 500 psi gauge, significantly increases the reaction selectivity for ethanol in the process.

We claim:
1. In a process for converting methanol to ethanol including contacting a mixture of methanol and cobalt catalyst with a gaseous mixture of carbon monoxide and hydrogen gas, in about a 1:2 carbon monoxide/hydrogen molar ratio, respectively, and allowing the combined mixtures to react at a temperature of about 175° C. to 240° C. and a pressure of about 3000–6000 psig., the improvement which comprises pre-pressurizing the methanol-cobalt catalyst mixture with an atmosphere consisting essentially of carbon monoxide in an amount corresponding to a pressure of about 10 to 1,000 psi gauge, at room temperature, or its equivalent at other temperatures, and maintaining said atmosphere of carbon monoxide while introducing said carbon monoxide/hydrogen gaseous mixture.

2. The improvement in accordance with claim 1 wherein the amount of carbon monoxide corresponds to a pressure of about 250 to 1,000 psi gauge at room temperature.

3. The improvement in accordance with claim 1 wherein the amount of carbon monoxide corresponds to a pressure of about 400 to 750 psi gauge at room temperature.

4. The improvement in accordance with claim 1 wherein said atmosphere of carbon monoxide contains up to about 10 volume percent of hydrogen gas.

* * * * *